US010603463B2

(12) United States Patent
Bollella

(10) Patent No.: US 10,603,463 B2
(45) Date of Patent: Mar. 31, 2020

(54) INDIVIDUAL WAKE-UP ALARM PATCH

(71) Applicant: LIFE PATCH INTERNATIONAL, Irvine, CA (US)

(72) Inventor: Donald Bollella, Irvine, CA (US)

(73) Assignee: LIFE PATCH INTERNATIONAL, Irvine, CA (US)

( * ) Notice: Subject to any disclaimer, the term of this patent is extended or adjusted under 35 U.S.C. 154(b) by 0 days.

(21) Appl. No.: 16/049,759

(22) Filed: Jul. 30, 2018

(65) Prior Publication Data

US 2019/0038867 A1  Feb. 7, 2019

Related U.S. Application Data

(60) Provisional application No. 62/540,126, filed on Aug. 2, 2017.

(51) Int. Cl.
*A61M 21/02* (2006.01)
*G08B 7/06* (2006.01)
(Continued)

(52) U.S. Cl.
CPC .......... *A61M 21/02* (2013.01); *A61M 21/00* (2013.01); *G04G 13/025* (2013.01); *G04G 21/04* (2013.01); *G08B 3/10* (2013.01); *G08B 7/06* (2013.01); *A61M 2021/0022* (2013.01); *A61M 2021/0027* (2013.01); *A61M 2021/0072* (2013.01); *A61M 2021/0083* (2013.01); *A61M 2205/18* (2013.01); *A61M 2205/3569* (2013.01);
(Continued)

(58) Field of Classification Search
None
See application file for complete search history.

(56) References Cited

U.S. PATENT DOCUMENTS 8,684,900 B2 * 4/2014 Tran ....................... A61B 8/488
600/3
8,688,189 B2 * 4/2014 Shennib ............... A61B 5/0006
600/382
(Continued)

FOREIGN PATENT DOCUMENTS

JP   2005-270401 A   10/2005
JP      3927495 B2    6/2007
(Continued)

OTHER PUBLICATIONS

Written Opinion of the Searching Authority for International Application No. PCT/US2018/043722, dated Jun. 5, 2019.
(Continued)

*Primary Examiner* — K. Wong
(74) *Attorney, Agent, or Firm* — Chang & Hale LLP

(57) ABSTRACT

Individual wake-up alarm patch. In some embodiments, a wearable patch can include a patch substrate configured to support a plurality of components, and to allow the patch to be attached to a skin of a user. The wearable patch can further include an alert component implemented at least partially within the patch substrate and configured to alert the user based on an alarm control signal. The wearable patch can further include a receiver circuit in communication with the alert component and configured to receive the alarm control signal and induce the alerting of the user by the alert component.

20 Claims, 12 Drawing Sheets

(51) Int. Cl.
*G08B 3/10* (2006.01)
*G04G 13/02* (2006.01)
*G04G 21/04* (2013.01)
*A61M 21/00* (2006.01)

(52) U.S. Cl.
CPC .............. *A61M 2205/3592* (2013.01); *A61M 2205/505* (2013.01); *A61M 2205/6054* (2013.01); *A61M 2209/06* (2013.01); *A61M 2209/088* (2013.01); *A61M 2210/0662* (2013.01)

(56) References Cited

U.S. PATENT DOCUMENTS 9,652,946 B2 *  5/2017  Ramstein ................. G08B 6/00
2007/0027388 A1  2/2007  Chou
2014/0121557 A1  5/2014  Gannon et al.

FOREIGN PATENT DOCUMENTS

JP          6067065  B2   1/2017
WO       2019023360  A2   1/2019

OTHER PUBLICATIONS

International Search Report for International Application No. PCT/US2018/043722, dated Jun. 5, 2019.
Written Opinion of the International Searching Authority for International Application No. PCT/US2018/043722, dated Jun. 5, 2019.

* cited by examiner

INDIVIDUAL WAKE-UP ALARM PATCH

CROSS-REFERENCE TO RELATED APPLICATION(S)

This application claims priority to U.S. Provisional Application No. 62/540,126 filed Aug. 2, 2017, entitled INDIVIDUAL WAKE-UP ALARM SYSTEM HAVING NON-INVASIVE PATCH, the disclosure of which is hereby expressly incorporated by reference herein in its respective entirety.

BACKGROUND

Field

The present disclosure relates to a wearable patch configured to provide an alarm functionality for a user.

Description of the Related Art

For a sleeping person, an alarm is often needed or desired at a set time to awake the person. In many situations, such an alarm can disturb another person sleeping nearby.

SUMMARY

In some teachings, the present disclosure relates to a wearable patch that includes a patch substrate configured to support a plurality of components, and to allow the patch to be attached to a skin of a user. The wearable patch further includes an alert component implemented at least partially within the patch substrate and configured to alert the user based on an alarm control signal. The wearable patch further includes a receiver circuit in communication with the alert component and configured to receive the alarm control signal and induce the alerting of the user by the alert component.

In some embodiments, the alert component can be implemented as a micro-transducer having a driver circuit and an alert element, the driver circuit can be configured to receive the alarm control signal and generate a drive signal for the alert element. The drive signal and the alert element can be configured to generate a sound output. The sound output can be provided with an intensity selected to awake the user from a sleeping state, but sufficiently low so that another sleeping person near the user is not awakened by the sound output.

In some embodiments, the drive signal and the alert element can be configured to generate a vibration output and/or an electrical output. In some embodiments, the drive signal and the alert element can be configured to generate an output having a uniform intensity, an output having a continuously varying intensity, or an output having a pattern of intensity pulses. The pattern of intensity pulses can include a plurality of periodic pulses having an approximately same intensity value, repeating sets of pulses with each set including a plurality of different intensity pulses, or a plurality of pulses having random or pseudo-random intensity values.

In some embodiments, the patch substrate can include an adhesive layer configured to allow the wearable patch to stick to the skin of the user. The patch substrate can be dimensioned to be worn, for example, on an arm of the user or an earlobe of the user.

In some embodiments, at least the receiver circuit can be implemented as an RFID (radio-frequency identification) circuitry.

According to some teachings, the present disclosure relates to a method for alerting a person. The method includes receiving, with a receiver of a wearable patch attached to a skin of the person, an alarm control signal. The method further includes generating, with a driver circuit, a drive signal in response to the control signal. The method further includes generating, with an alert element, an output configured to be sensed the person to thereby alert the person.

In some embodiments, the method can further include attaching the wearable patch to the person prior to the receiving.

In some embodiments, the method can further include generating the alarm control signal. Such generating of the control signal can be achieved by a control unit. Such a control unit can be a device external to the wearable patch.

In some embodiments, the output can include a sound output and/or a vibrational output.

In some implementations, the present disclosure relates to a system for alerting a person. The system includes a wearable patch configured to be attached to a skin of the person and alert the person with an output based on an alarm control signal, and a control unit configured to generate and transmit the alarm control signal to the wearable patch.

In some embodiments, the wearable patch can include an RFID (radio-frequency identification) circuitry configured to receive the alarm control signal from the control unit. The wearable patch can further include a micro-transducer configured to generate the output based on the alarm control signal. The micro-transducer can include an alert element configured to generate the output. The output can include either or both of a sound output and a vibrational output.

In some embodiments, the control unit can be implemented as a dedicated device associated with the wearable patch, or as an application software operating in a wireless device such as a smartphone.

In some implementations, the present disclosure relates to a kit for alerting a person. The kit includes a plurality of wearable patches implemented in a packaged format, with each wearable patch including a patch substrate configured to support a plurality of components, and to allow the patch to be attached to a skin of a user. The wearable patch further includes an alert component implemented at least partially within the patch substrate and configured to alert the user based on an alarm control signal. The wearable patch further includes a receiver circuit in communication with the alert component and configured to receive the alarm control signal and induce the alerting of the user by the alert component. The kit further includes a printed instruction configured to facilitate use of the wearable patch on the person.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

DETAILED DESCRIPTION OF SOME EMBODIMENTS

The headings provided herein, if any, are for convenience only and do not necessarily affect the scope or meaning of the claimed invention.

Disclosed are examples related to systems, methods and devices for providing wake-up alarm functionality for an individual without disturbing another person sleeping nearby. When an individual sleeps and desires to wake up at a certain time, he/she typically sets an alarm, usually an audible alarm, to be triggered at or near that time. Such an alarm may allow the individual to "snooze" one or more times, thereby making the wake-up process more gradual.

When that individual is sleeping with another person (e.g., in the same bed), or in near proximity to another sleeping person (e.g., in a dormitory), the audible alarm typically disrupts the sleep of the other person. Such a disruption of the sleep of the other person is generally not desirable.

Figure 1:
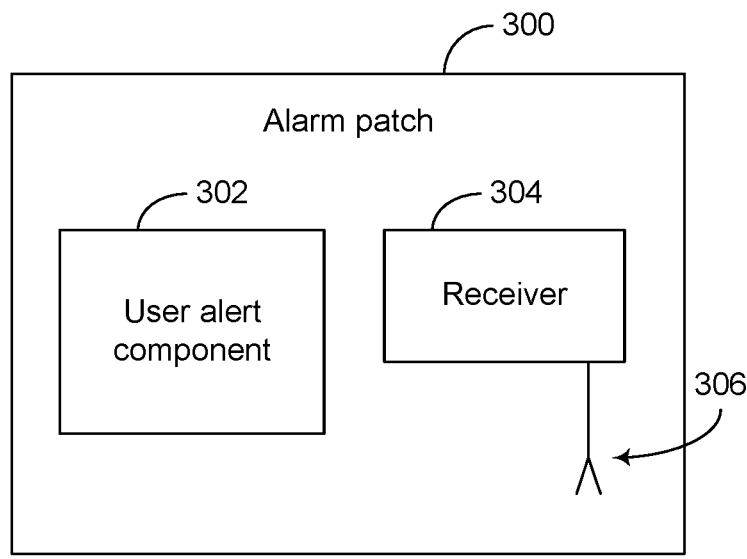
FIG. 1 depicts an alarm patch that can be worn by a person during activities such as sleep.

FIG. 1 depicts a non-invasive patch device 300 that can be worn by a person during activities such as sleep. Although various examples are described herein in the context of sleep, it will be understood that one or more features of the present disclosure can also be utilized in other activities.

FIG. 1 shows that in some embodiments, the non-invasive patch 300 can include a user alert component 302 and a receiver 304 configured to receive an alarm control signal for the user alert component 302. Such reception of the alarm control signal can be facilitated by an antenna 306 in communication with the receiver 304.

Figure 2:
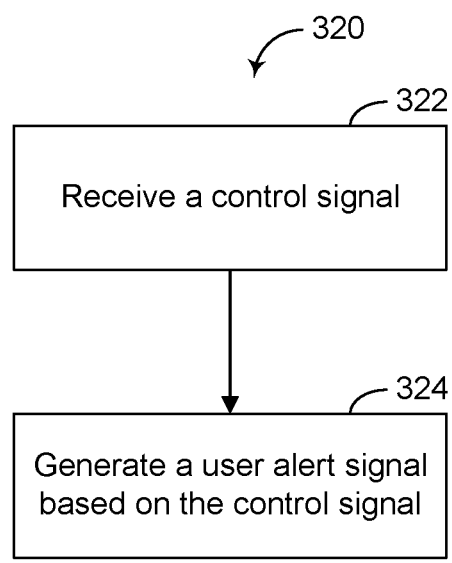
FIG. 2 shows a process that can be implemented by the alarm patch of FIG. 1.

FIG. 2 shows a process 320 that can be implemented by the non-invasive patch 300 of FIG. 1. In block 322, an alarm control signal can be received. In block 324, a user alert signal can be generated based on the alarm control signal. In some embodiments, such a user alert signal can be generated by the non-invasive patch 300 and thereby be applied to the user to alert (e.g., wake-up) the user.

Figure 3:
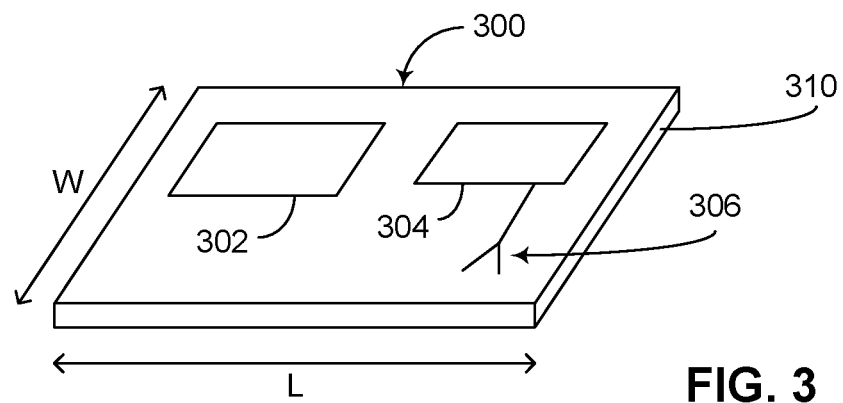
FIG. 3 shows that in some embodiments, an alarm patch can have a generally rectangular shape.
Figure 4:
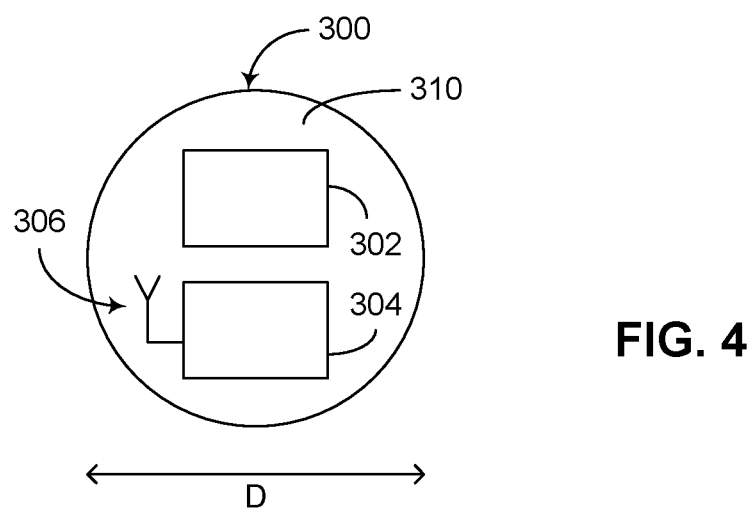
FIG. 4 shows that in some embodiments, an alarm patch can have an elliptical shape, such as a circular shape.

FIGS. 3 and 4 show non-limiting examples of how a non-invasive patch 300 can be implemented in different form factors. For example, FIG. 3 shows that in some embodiments, a non-invasive patch 300 can have a generally rectangular shape with a length L and a width W. Such dimensions can be selected to, for example, allow application of the patch 300 on an area of the user with sufficient space (e.g., on an arm). By way of examples, the length L can be 2 to 4 inches, and the width W can be 1 to 2 inches.

In another example, FIG. 4 shows that in some embodiments, a non-invasive patch 300 can have an elliptical shape, such as a circular shape, with a diameter D. Such a dimension can be selected to, for example, allow application of the patch 300 on a smaller area of the user that is more discreet and/or more sensitive to low-intensity vibration and/or audio stimulation (e.g., on an earlobe). By way of an example, the diameter D can be ⅛ to ½ inch.

It will be understood that a non-invasive patch 300 having one or more features as described herein can be implemented with other shapes.

In the examples of FIGS. 3 and 4, each non-invasive patch 300 can include a patch substrate 310 configured to provide wearable functionality and to support a number of components. Examples related to such wearable functionality and support functionality can be found in U.S. Pat. No. 9,133,024 titled PERSONAL DIAGNOSTIC DEVICES INCLUDING RELATED METHODS AND SYSTEMS, which is expressly incorporated by reference in its entirely, and its disclosure is to be considered part of the specification of the present application.

In the examples of FIGS. 3 and 4, each non-invasive patch 300 is shown to include a user alert component 302, a receiver 304, and an antenna 306, similar to the example of FIG. 1. In some embodiments, at least the receiver portion of the patch 300 can include an RFID (radio-frequency identification) circuitry configured to facilitate, for example, a transfer of an alarm control signal from a device to the patch 300.

Figure 5:
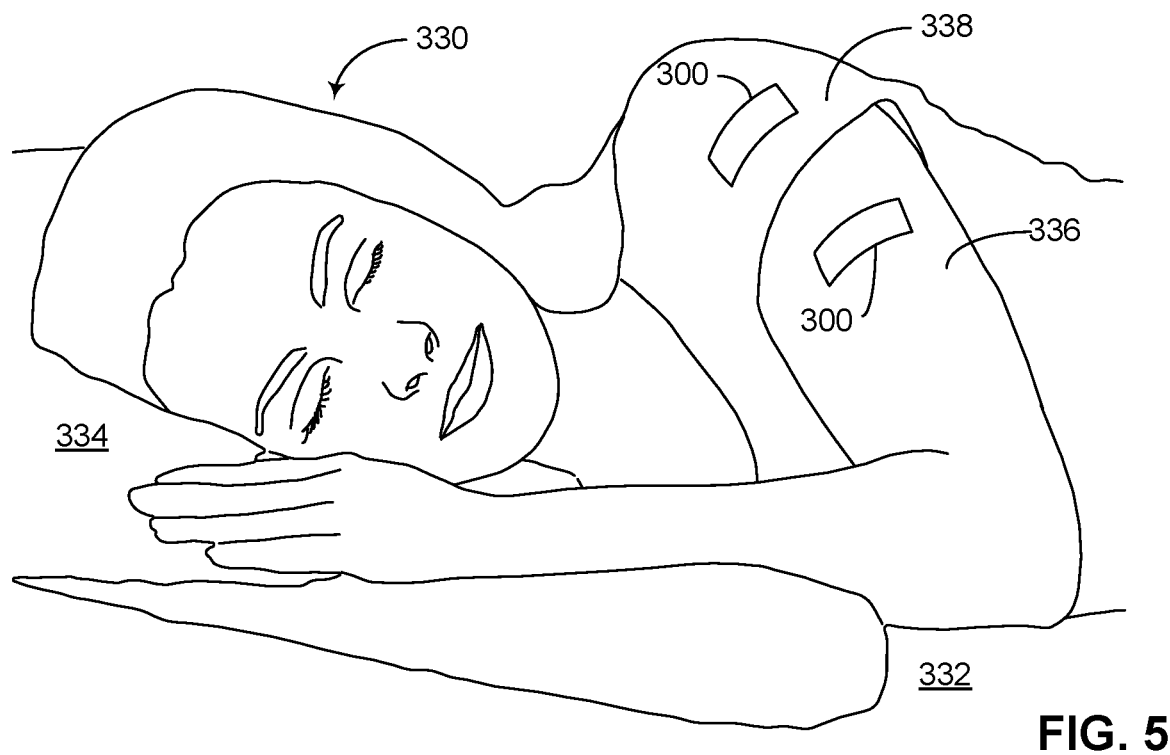
FIG. 5 shows a person sleeping on a bed and wearing an alarm patch having one or more features as described herein.

FIG. 5 shows a person 330 sleeping on a bed 332 with her head supported by a pillow 334. FIG. 5 further shows that such a sleeping person can wear a non-invasive patch 300 having one or more features as described herein at one or more locations. For example, a non-invasive patch 300 can be configured to be worn on an exposed skin of an arm 336. In another example, a non-invasive patch 300 can be configured to be worn on a surface of a clothing item 338 that is sufficiently close to the skin. In some embodiments, the non-invasive patch(es) 300 worn by the user 330 can have a larger form factor such as the example of FIG. 18.

Figures 6A, 6B:
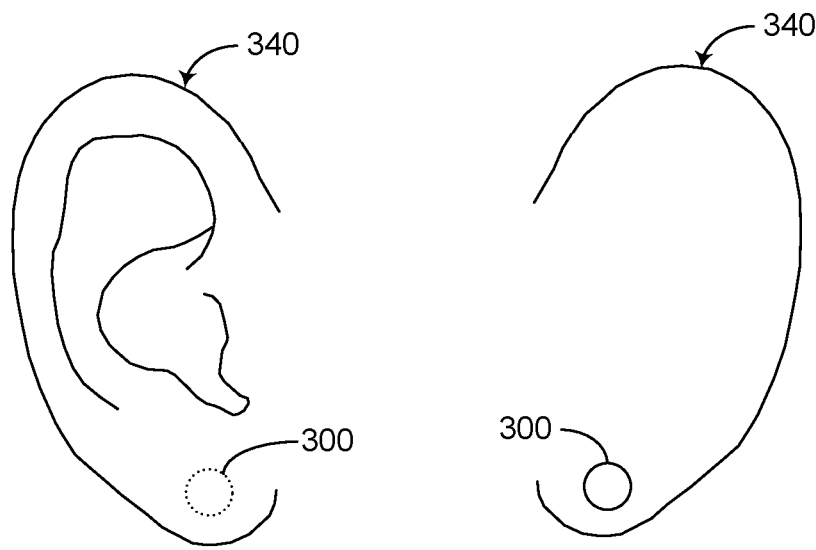
FIGS. 6A and 6B show that in some embodiments, an alarm patch having one or more features as described herein can be configured to be worn on a smaller portion of a user.

FIGS. 6A and 6B show that in some embodiments, a non-invasive patch 300 having one or more features as described herein can be configured to be worn on a smaller portion of a user (e.g., the sleeping person in FIG. 5). For example, the non-invasive patch 300 is shown to be worn on the surface of an earlobe on the back side of an ear 340. FIG. 6A depicts the front side (visible side) of the ear 340, and FIG. 6B depicts the back side (generally hidden side) of the ear 340.

It will be understood that a non-invasive patch 300 having one or more features as described herein can be worn at other parts of a user.

Figure 7:
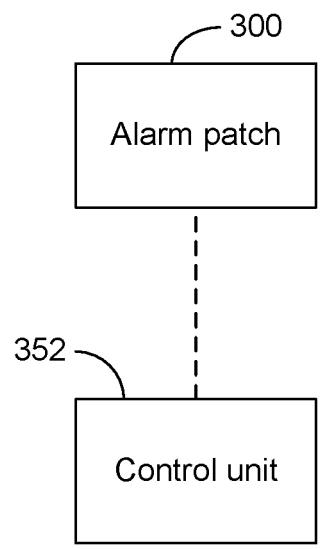
FIG. 7 depicts a block diagram of a system that can include an alarm patch having one or more features as described herein.

FIG. 7 depicts a block diagram of a system that can include a non-invasive patch 300 having one or more features as described herein. In some embodiments, such a system can also include an external control unit 352 configured to communicate with the non-invasive patch 300 to, for example, provide an alarm control signal.

Figure 8:
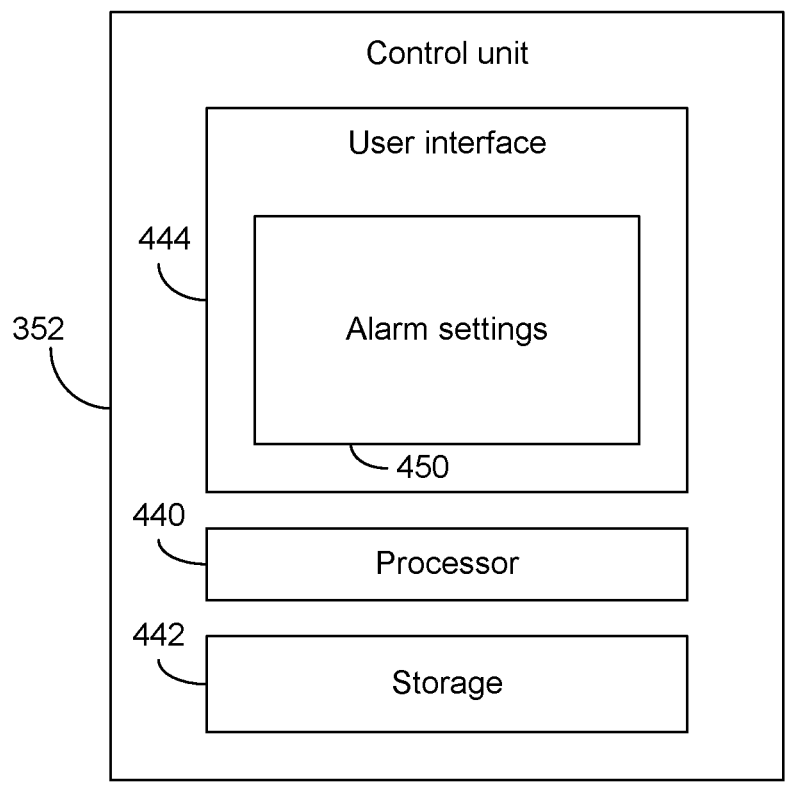
FIG. 8 depicts a control unit that can be utilized in the system of FIG. 7.

FIG. 8 depicts a control unit 352 that can be utilized as the control unit 352 of the system of FIG. 7. In some embodiments, the control unit 352 of FIG. 8 can include a user interface 444 configured to allow a user to control one or more functionalities associated with a corresponding alarm patch (e.g., 300 in FIG. 7). Such functionalities can include, for example, turning alarm ON or OFF, setting of alarm time, setting of alert tone and/or intensity, etc. In the example of FIG. 8, some or all of such alarm functionalities can be facilitated by an alarm settings component 450 of the user interface 444.

As further shown in the example of FIG. 8, the control unit 352 can include a processor 440; and such a processor can provide and/or facilitate some or all of the foregoing control functionalities. The control unit 352 can further include a memory or storage component 442 (e.g., a non-transitory computer readable medium); and such a storage component can store information such as alarm settings.

In some embodiments, the control unit 352 of FIG. 8 can be implemented as a dedicated device configured for operation with one or more alarm patches. Such a dedicated device can generate alarm control signals compatible with and understood by the corresponding alarm patch(es).

In some embodiments, the control unit 352 of FIG. 8 can be implemented as an application software (also referred to as an app) running on a device such as a smartphone. Similar to the dedicated device described above, the application software can be configured to generate alarm control signals for one or more alarm patches.

Figure 9:
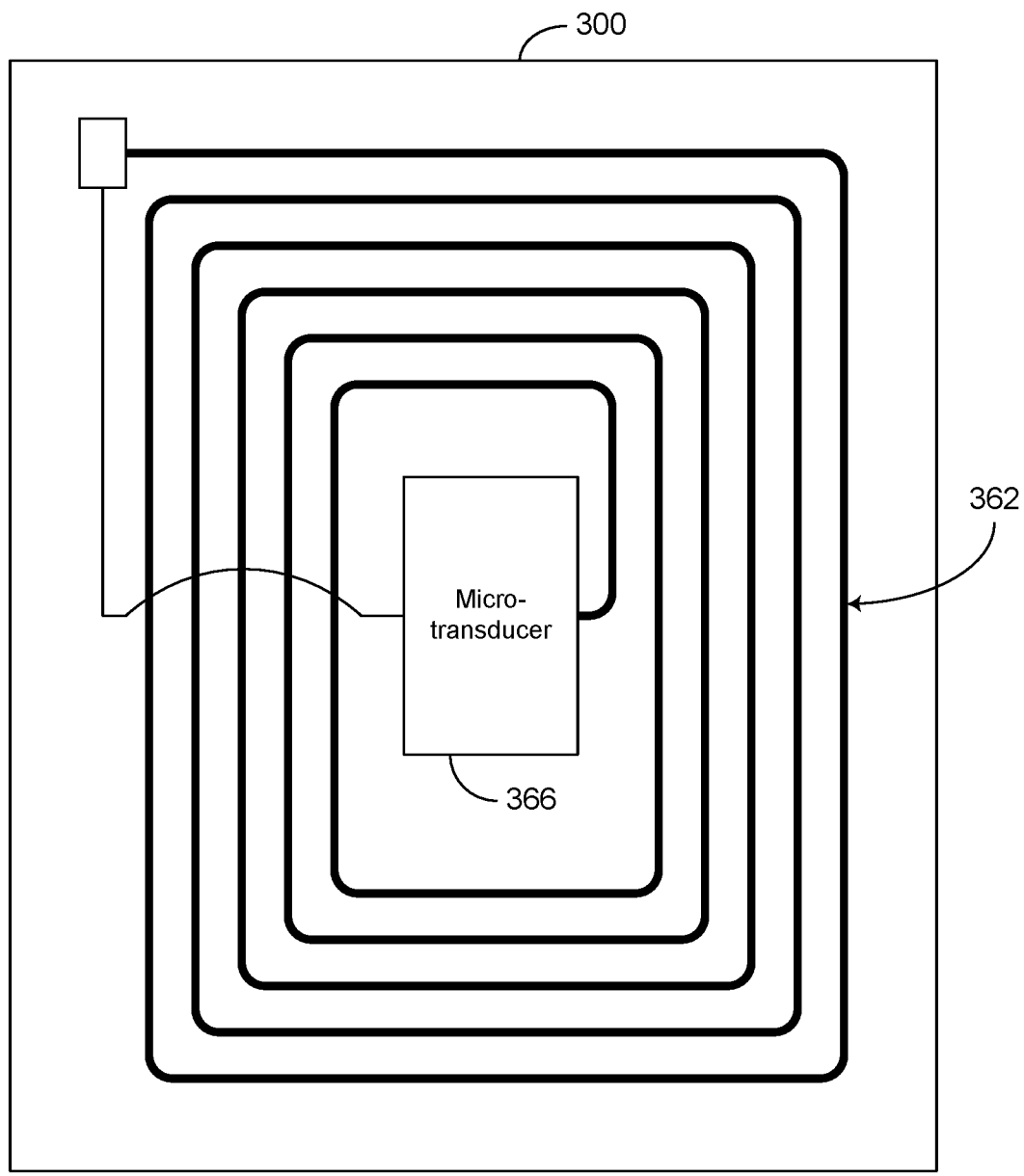
FIG. 9 shows an example of how such an RFID (radio-frequency identification) circuitry can be implemented in an alarm patch.

In some embodiments, at least a portion of a non-invasive patch (also referred to herein as an alarm patch) having one or more features as described herein can be implemented as a passive device utilizing, for example, RFID (radio-frequency identification) circuitry. FIG. 9 shows an example of how such an RFID circuitry can be implemented in an alarm patch 300. For example, a coil 362 can be provided to allow collection of electromagnetic energy transmitted from an external device such as a control unit (e.g., 352 in FIGS. 7 and 8). Such a coil can also be configured to function as an antenna (e.g., 306 in FIGS. 1, 3 and 4).

FIG. 9 shows that the energy pickup coil/antenna 362 can be connected to a micro-transducer 366. In some embodiments, such a micro-transducer can be configured to be powered at least partially by the energy picked up by the coil 362 and be activated based on a control signal received by the antenna 362. The control signal may or may not be part of the electromagnetic energy transmitted from the control unit.

Figure 10:
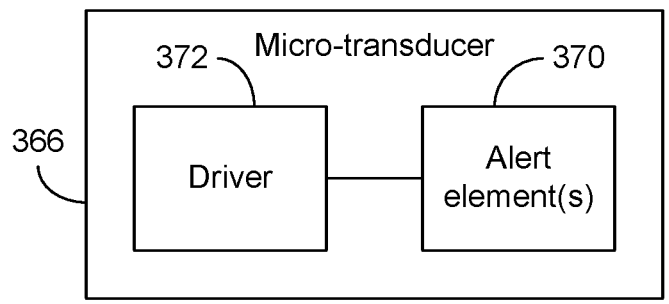
FIG. 10 shows that in some embodiments, a micro-transducer having a driver circuit and one or more alert elements can be utilized in an alarm patch.

FIG. 10 shows that in some embodiments, the micro-transducer 366 of FIG. 9 can include a driver circuit 372 and one or more alert elements 370. The driver circuit 372 can be configured to receive the control signal and power and drive the alert element(s) 370 to thereby awake the user with an alarm.

Figure 11A:
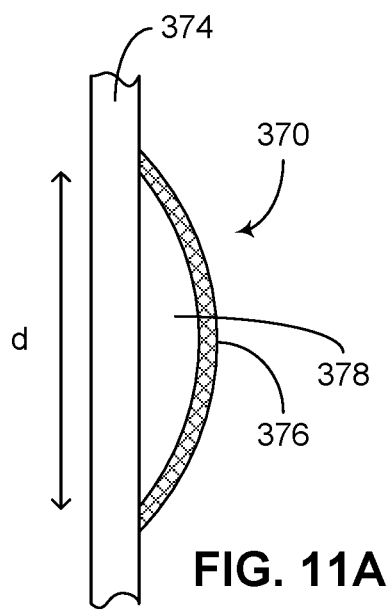
FIGS. 11A, 11B, 11C and 11D show non-limiting examples of an alarm element that can be utilized in the micro-transducer of FIG. 10.

FIGS. 11A-11D show non-limiting examples of an alarm element 370 that can be utilized in the micro-transducer 366 of FIG. 10. For example, FIG. 11A shows that in some embodiments, an alarm element 370 can include a micro-speaker element 376 coupled to a substrate layer 374. In some embodiments, such a substrate layer can be configured to engage the user (e.g., on the skin) directly or through an intermediate layer.

In some embodiments, the micro-speaker element 376 can be configured as, for example, a semi-shell dimensioned to provide a micro-sound chamber 378. Such a micro-sound chamber can be dimensioned (e.g., diameter d of approximately ⅛ to ½ inch) appropriately, and along with the drive signal provided by the driver 372, the micro-speaker element 376 can provide a sound signal with a desired range of frequency to the user. In many applications, the proximity of the alarm patch to the user's ear and/or skin can allow such a sound signal to have low intensity to wake the user, but not disturb another person.

Figure 11B:
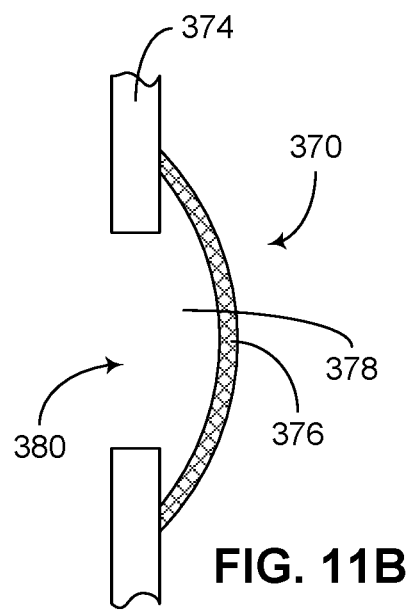

In the example of FIG. 11A, the micro-sound chamber 378 can be configured to be substantially enclosed by the micro-speaker element 376 and the substrate layer 374. FIG. 11B shows that in some embodiments, a micro-sound chamber 378 can be partially open. For example, an opening 380 can be provided on the substrate layer 374. Such an opening can allow the sound signal to be provided by the micro-speaker element 376 without having to pass through the substrate layer 374.

Figure 11C:
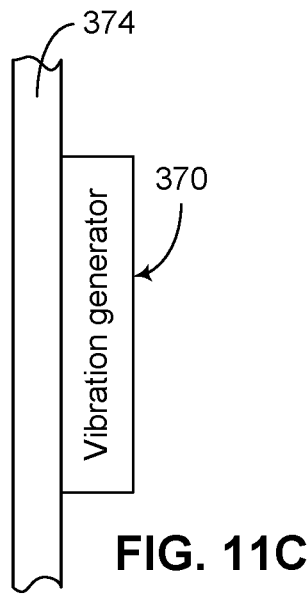

FIG. 11C shows that in some embodiments, an alarm element 370 can include a vibration generator coupled to a substrate layer 374. In some embodiments, such a substrate layer can be configured to engage the user (e.g., on the skin) directly or through an intermediate layer. Such a vibration generator can be driven by the drive signal provided by the driver 372. In many applications, the proximity of the alarm patch to the user's ear and/or skin can allow the resulting vibration to have low intensity and yet wake the user, but not disturb another person.

Figure 11D:
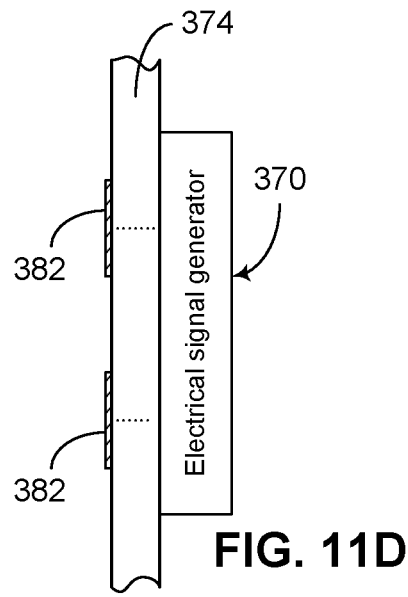

FIG. 11D shows that in some embodiments, an alarm element 370 can include an electrical signal generator coupled to a substrate layer 374. In some embodiments, such a substrate layer can be configured to include electrodes 382 for engaging the user (e.g., on the skin). Such an electrical signal generation can be driven by the drive signal provided by the driver 372. In many applications, the proximity of the alarm patch to the user's ear and/or skin can allow the resulting electrical signal to have low power and yet wake the user, but not disturb another person.

FIGS. 12A-12E show non-limiting examples of sound profiles that can be generated by the micro-transducer 366 of FIG. 10. As described herein, such sound can be generated by the alert element 370 based on a drive signal provided by the driver 372.

Figure 12A:
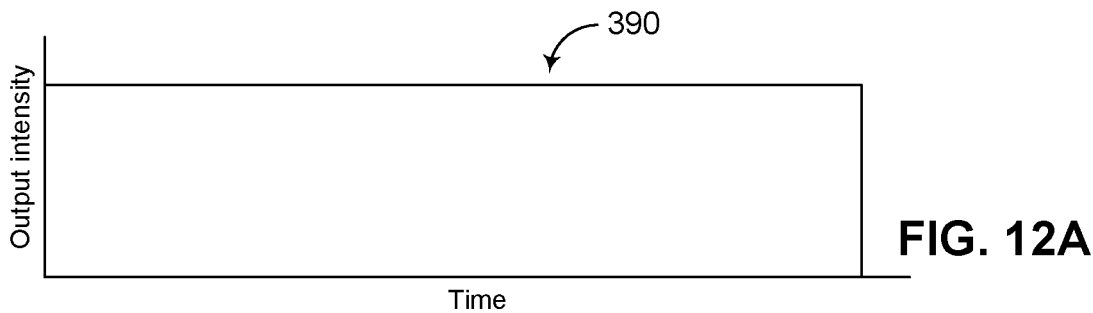
FIGS. 12A, 12B, 12C, 12D and 12E show non-limiting examples of sound profiles that can be generated by the micro-transducer of FIG. 10.

FIG. 12A shows that in some embodiments, a sound profile 390 can include a generally uniform intensity. In some embodiments, such sound can be produced for a pre-determined period of time, or be produced until stopped by a user (e.g., through the corresponding control unit).

Figure 12B:
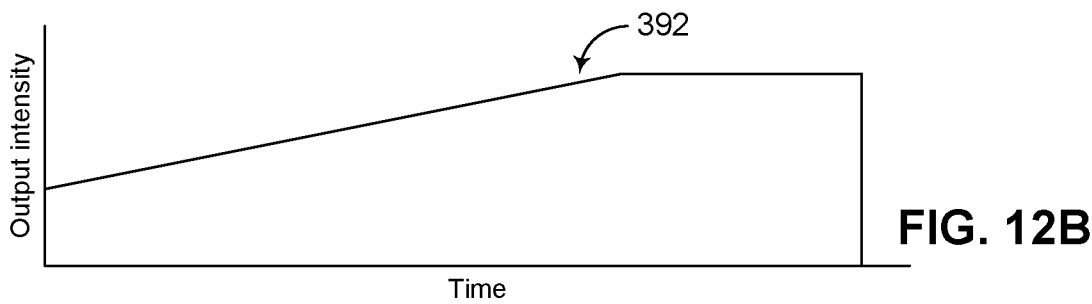

FIG. 12B shows that in some embodiments, a sound profile 392 can include an intensity that changes gradually. For example, a sound can be generated initially at a low intensity, and its intensity can increase gradually until the intensity reaches an upper limit. Such sound intensity at the upper limit can remain on for a pre-determined period of time, or until stopped by a user (e.g., through the corresponding control unit).

Figure 12C:
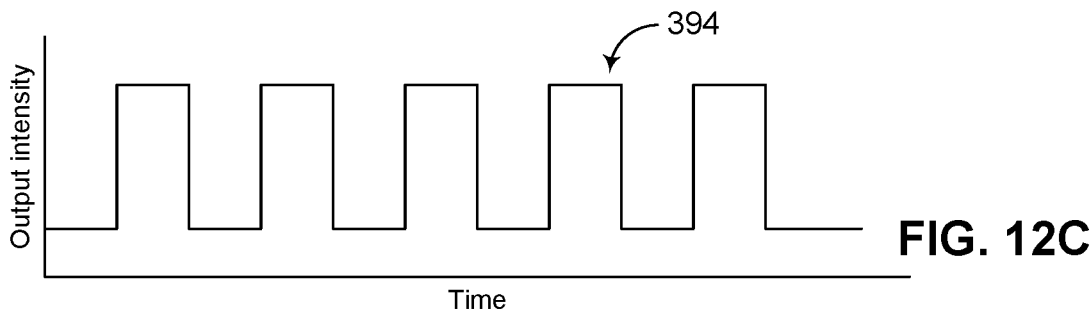
Figure 12D:
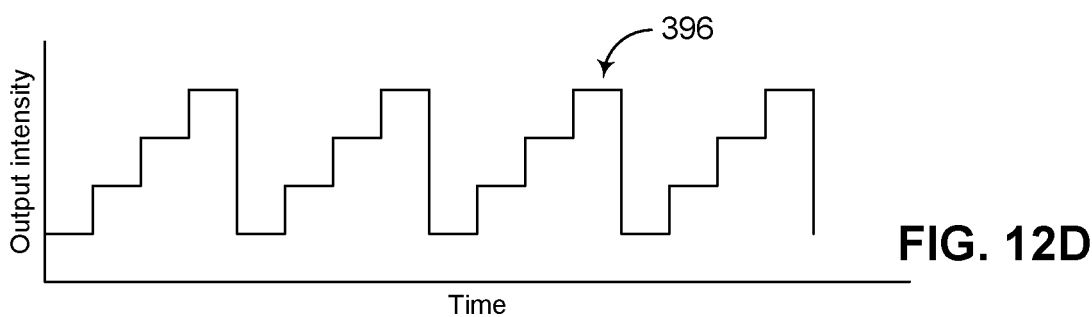
Figure 12E:
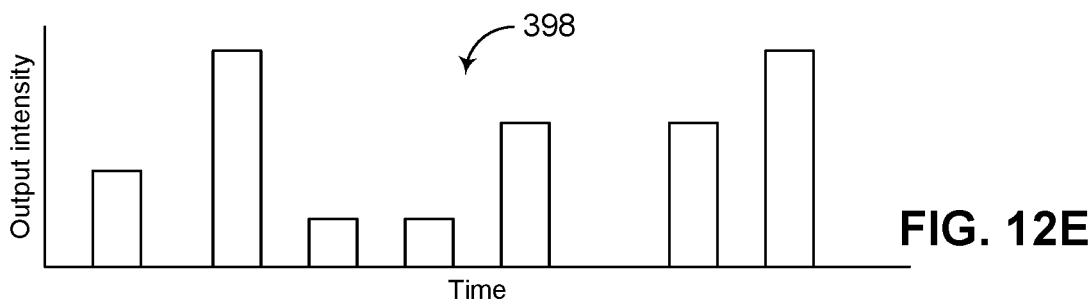

FIGS. 12C-12E show that in some embodiments, sound profiles can include pulses of intensity values. For example, FIG. 12C shows that a sound profile 394 can include sound pulses having similar intensity. In another example, FIG. 12D shows that a sound profile 396 can include repetition of a pattern of sound pulses (e.g., a pattern having step-increased intensity values). In yet another example, FIG. 12E shows that a sound profile 398 can include sound pulses having random (or pseudo-random) intensity values. Each of the example sound profiles of FIGS. 12C-12E can remain on for a pre-determined period of time, or until stopped by a user (e.g., through the corresponding control unit).

It will be understood that other sound profiles can also be implemented. It will also be understood that vibration profiles can be generated in similar manners.

Figure 13:
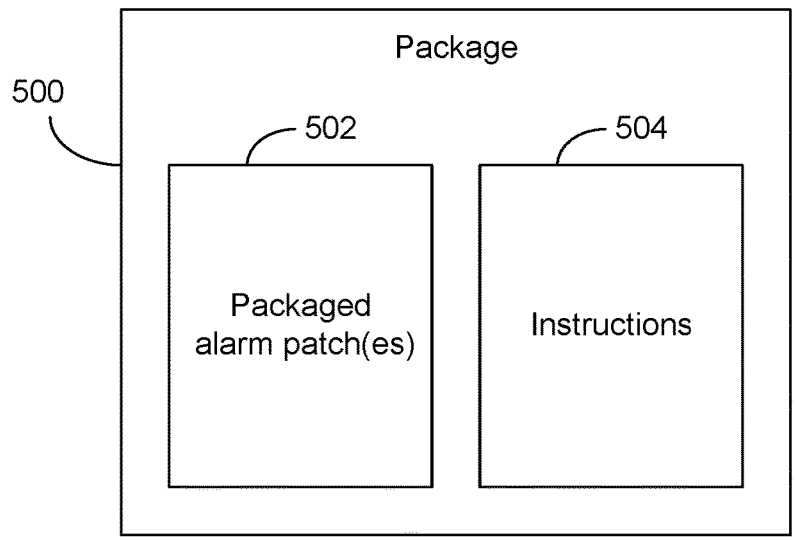
FIG. 13 shows that in some embodiments, one or more alarm patches having one or more features as described herein can be in a packaged format for easier use by a user.

FIG. 13 shows that in some embodiments, one or more patches having one or more features as described herein can be in a packaged format 502 for easier use by a user. Such a packaged format of patch(es) can be included in, for example, a packaged product 500. In some embodiments, the packaged product 500 can also include an instruction 504 such as a printed instruction. Such an instruction can provide information on, for example, proper and/or recommended application of the included patch(es).

Figure 14:
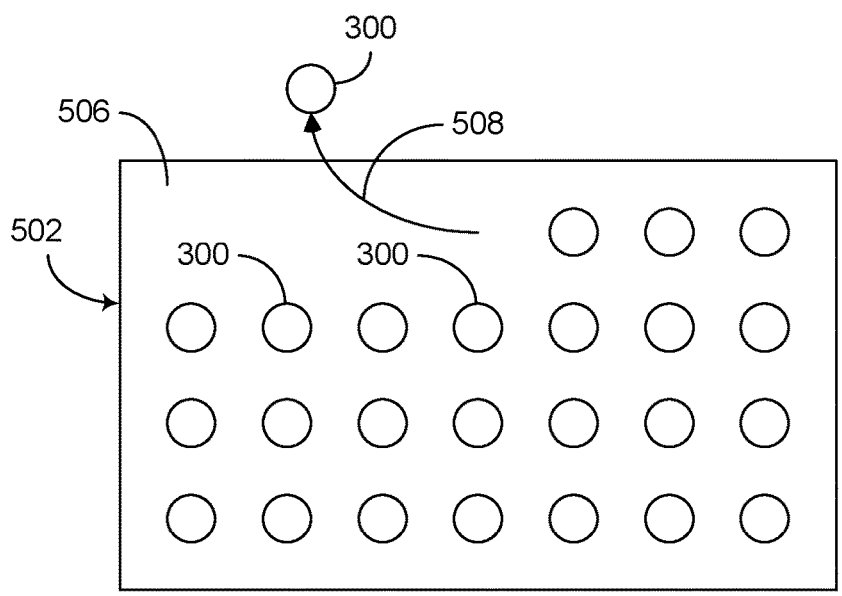
FIG. 14 shows an example of a packaged format having a support sheet with a plurality of patches secured thereto.

FIG. 14 shows an example of a packaged format 502 having a support sheet 506 with a plurality of patches 300 secured thereto. Such number of patches can allow a user to remove (arrow 508) a patch 300 from the support sheet 506 for use whenever a wake-up alarm is desired (e.g., to be awakened from sleep). In some applications, such use of patches can be performed for an unspecified number of days, only as needed or desired, for a specified number of days to build a wake-up profile of the user, or any combination thereof.

Figure 15:
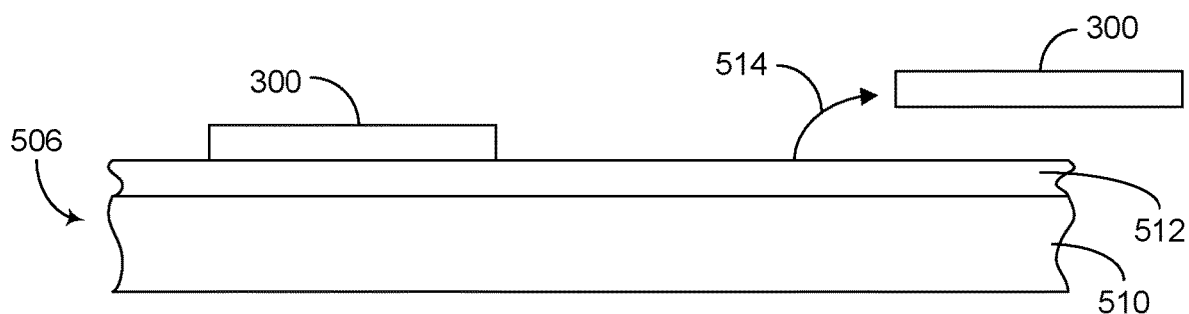
FIG. 15 shows an enlarged side sectional view of an example support sheet that can be utilized to hold, until removal, a plurality of patches, similar to the example of FIG. 14.

FIG. 15 shows an enlarged side sectional view of an example support sheet 506 that can be utilized to hold (until removal) a plurality of patches, similar to the example of FIG. 14. In some embodiments, the support sheet 506 can include a base layer 510 (e.g., paper, plastic, etc.) and a release layer 512. The release layer 512 can be secured to the base layer 510, and be configured to securely hold the patches 300 thereon during transport and storage phases. Assuming that a patch includes an adhesive layer for application onto the skin of a user, the release layer can further be configured to allow the patch to be removed (e.g., peeled off) cleanly for application onto the user. In the example of FIG. 15, such removal of the patch 300 from the release layer 512 is depicted as an arrow 514.

In some embodiments, it may be desirable to activate a patch at an appropriate time (e.g., when removed from a release layer or when applied to the skin of a user). For example, such an activation can include a hand-shake pairing process between the patch and a control unit. In some embodiments, such a hand-shake paring process can be initiated when a patch is removed from a release layer, and when the patch is in appropriate proximity to a control unit.

In some embodiments, a control unit having one or more features as described herein can be configured to provide a calibration functionality. Such a calibration functionality can allow, for example, control signals to provide more personalized alarm settings.

Figure 16:
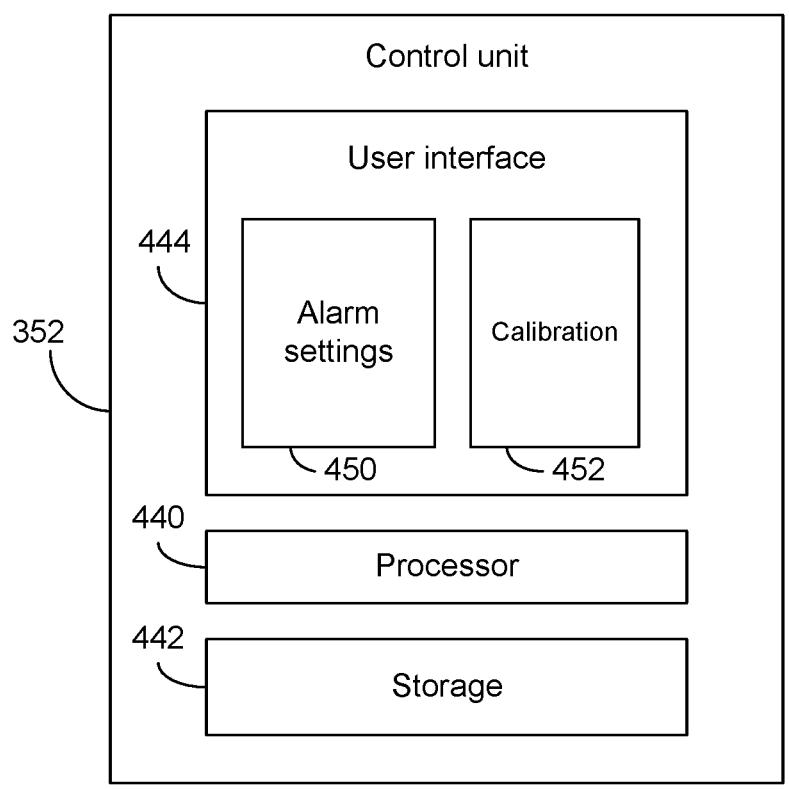
FIG. 16 depicts a control unit that includes a user interface component for controlling operation of an alarm patch.

FIG. 16 depicts a control unit 352 that includes a user interface 444. Such a user interface can include an alarm settings component 450, and a calibration component 452. Such a calibration component can be based on information obtained from a user.

By way of examples, suppose that the user selects a particular type of sound intensity pattern (e.g., as in the examples of FIGS. 12A-12E). Such sound intensity patterns can include a default intensity setting for maximum intensity values. Such maximum intensity value for a given sound pattern may be too high for some users, suitable for some other users, and too low for yet other users. Accordingly, the calibration component 452 of the control unit 352 can allow the user to provide a feedback on the loudness of the selected sound pattern. Based such input, the control unit 352 can adjust the intensity level of the selected sound pattern.

As further shown in the example of FIG. 16, the control unit 352 can include a processor 440; and such a processor can provide and/or facilitate some or all of the foregoing control and calibration functionalities. The control unit 352 can further include a memory or storage component 442 (e.g., a non-transitory computer readable medium); and such a storage component can store information such as initial settings, user feedback inputs, etc.

Figure 17:
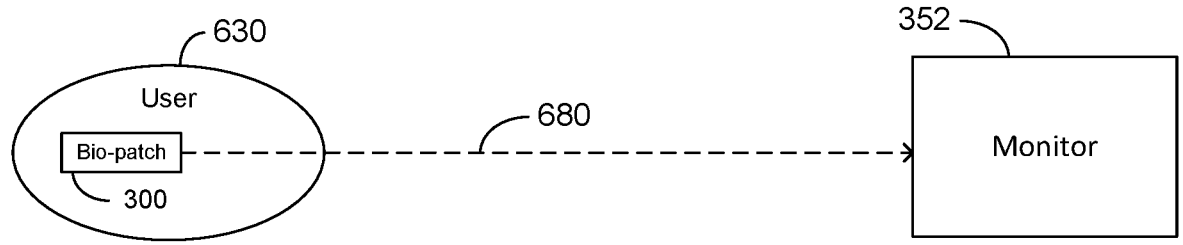
FIG. 17 shows an example of a communication functionality that can be implemented for a patch.

As described herein, a patch having one or more features as described herein can include a communication component to facilitate transmission of information such as sensor data, and/or to facilitate reception of information such as alarm settings. FIG. 17 shows an example of a system that can be implemented to utilize such a communication functionality. For example, a patch 300 having one or more features as described herein is shown to be worn by a user 630. Information transmitted (e.g., in a wireless manner) is depicted as 680, and such information can be received by a monitor 352 (also referred to herein as a control unit). Such a monitor can include a receiver circuit configured to process the received signal from the patch 300. The monitor 352 can further include a processor to support various functionalities as described herein.

Figure 18:
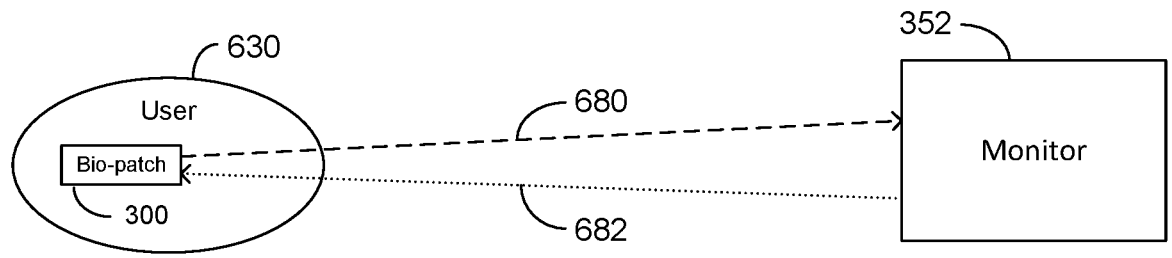
FIG. 18 shows an example of a communication functionality in which a patch can include transmit and receive capabilities.

In some embodiments, a patch having one or more features as described herein can also include a receiver circuit to allow the patch to receive information such as instructions, diagnostics, etc. Accordingly, FIG. 18 shows an example of a system that can be implemented to utilize such transmit and receive functionalities. For example, a patch 300 having one or more features as described herein is shown to be worn by a user 630. Information transmitted (e.g., in a wireless manner) is depicted as 680, and such information can be received and processed by a monitor 352, similar to the example of FIG. 17.

In the example of FIG. 18, the patch 300 can also receive information (indicated as 682). Such received information can be achieved in a wireless mode, a wire mode, or any combination thereof. Although such information is depicted as being provided by the monitor 352, it will be understood that information provided to the patch 300 may or may not be from the same component (e.g., monitor in FIG. 18).

Figure 19:
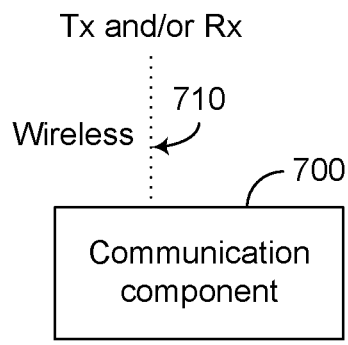
FIG. 19 shows that in some embodiments, a patch can be configured to communicate with another device in a wireless manner.
Figure 20:
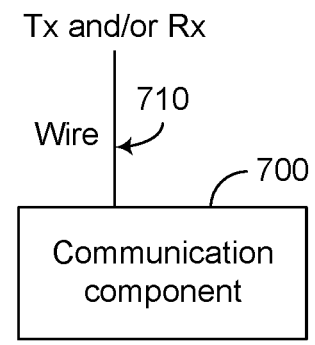
FIG. 20 shows that in some embodiments, a patch can be configured to communicate with another device through a wire.

FIGS. 19-23 show examples of communications and/or system functionalities that can be implemented in a system having one or more patches as described herein. For example, FIGS. 19 and 20 show that in some embodiments, a communication component 700 (e.g., 304 in FIG. 1) of a patch can be configured to provide a wireless communication (depicted as 710 in FIG. 19) with an external device, a wired communication (depicted as 710 in FIG. 20) with an external device, or some combination thereof. For the purpose of description of FIGS. 19 and 20, an external device can be another patch, a non-patch device, etc.

In some embodiments, in each of the examples of FIGS. 19 and 20, the wireless and/or wired communication link 710 can include a transmit (Tx) functionality (relative to the corresponding patch), a receive (Rx) functionality, or any combination thereof.

Figure 21:
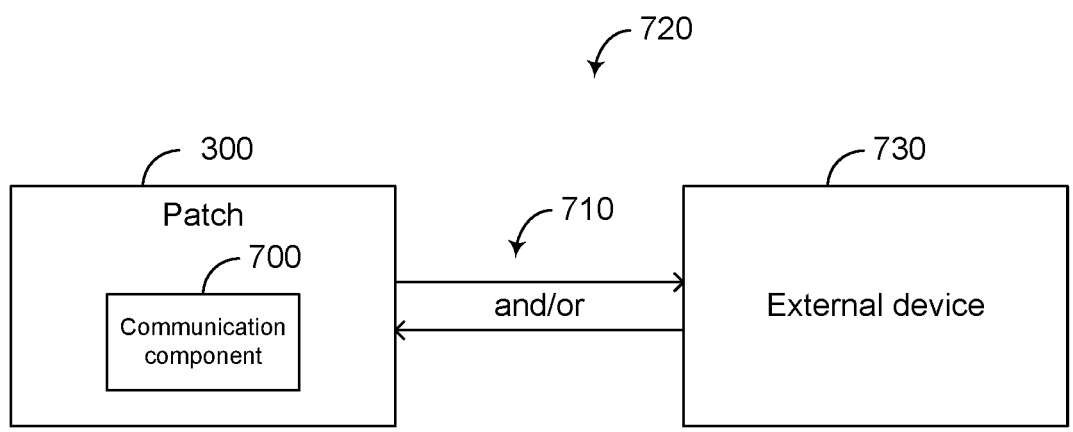
FIG. 21 shows that in some embodiments, a patch and an external device can be in a system and communicate with each other.

FIG. 21 shows a system 720 that can be formed with one or more patches 300 as described herein, and an external device 730. For the purpose of description of FIG. 21, it will be understood that the external device 730 is relative to the patch 300. Thus, if the external device 730 is another patch, then the patch 300 shown in FIG. 21 can be considered to be external to the other patch (730). As described in reference to FIGS. 19 and 20, it will be understood that the external device 730 can be a patch that may or may not be similar to the patch 300.

In the example of FIG. 21, the patch 300 is shown to include a communication component similar to the examples of FIGS. 19 and 20. Accordingly, the communication between the patch 300 and the external device 730 can include transmit and/or receive portions.

Figure 22:
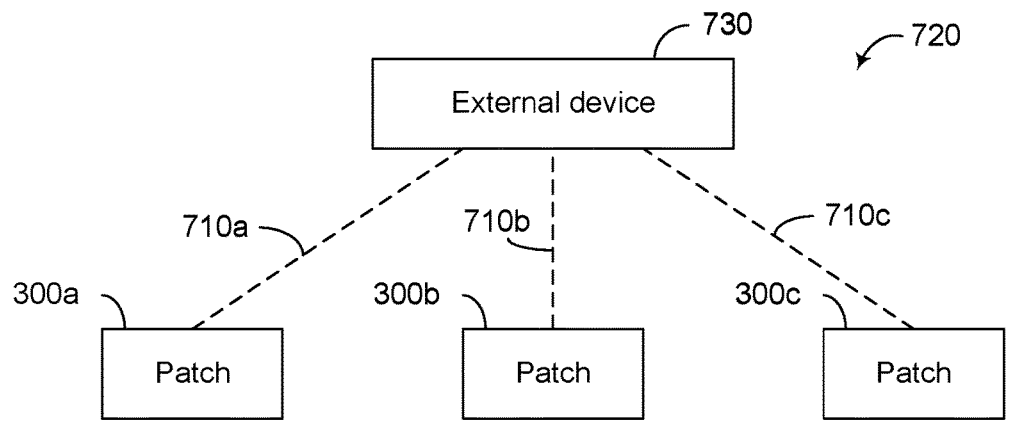
FIG. 22 shows that in some embodiments, the system of FIG. 21 can include a plurality of patches that communicate with a common external device.

FIG. 22 shows that in some embodiments, the system 720 of FIG. 21 can include a plurality of patches 300 that communicate with a common external device. For example, a system 720 of FIG. 22 is shown to include a plurality of patches 300a, 300b, 300c and an external device 730. More particularly, the first patch 300a can be in communication (710a) with the external device 730, the second patch 300b can be in communication (710b) with the external device 730, and the third patch 300c can be in communication (710c) with the external device 730. In some embodiments, such an external device can be configured to, for example, coordinate operations of the patches (300a, 300b, 300c), collect data from the patches, etc. In some embodiments, the external device 730 can be configured to communicate with another device at a similar level, with another device at a higher level, or any combination thereof.

Figure 23:
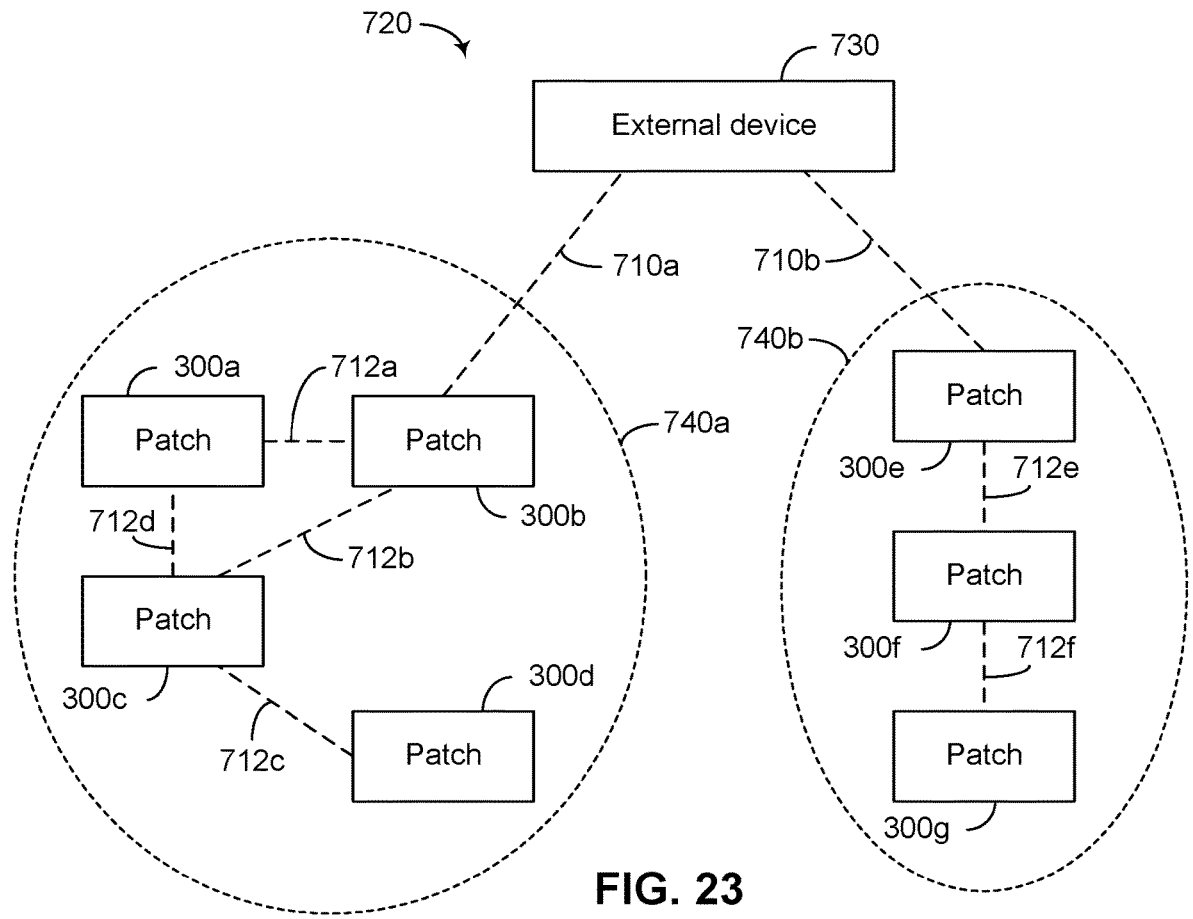
FIG. 23 shows that in some embodiments, the system of FIG. 21 can include a plurality of patches that can communicate with each other, and/or with an external device.

FIG. 23 shows that in some embodiments, the system 720 of FIG. 21 can include a plurality of patches 300 that can communicate with each other, and/or with an external device. For example, a first group (740a) of patches and a second group (740b) are shown to be included in a system 720, and generally in communication with an external device 730. More particularly, the first group 740a is shown to include four example patches 300a, 300b, 300c, 300d, and the second group 740b is shown to include three example patches 300e, 300f, 300g. Such first and second groups 740a, 740b of patches can be grouped based on, for example, physical proximity/separation, different functionalities, etc.

In some embodiments, within a given group, each of the plurality of patches can communicate directly with the external device 730, through a representative patch, or some combination thereon. For example, for the first group 740a, the patches 300a and 300b are shown to have a communication link 712a; the patches 300a and 300c are shown to have a communication link 712d; the patches 300c and 300d are shown to have a communication link 712c; and the patches 300c and 300b are shown to have a communication link 712b. Further, the patch 300b is shown to be a representative communication member and be in communication (710a) with the external device 730.

In another example, for the second group 740b, the patches 300e and 300f are shown to have a communication link 712e; and the patches 300f and 300g are shown to have a communication link 712f. Further, the patch 300e is shown to be a representative communication member and be in communication (710b) with the external device 730.

In some embodiments, the communication links between the patches within a given group can be based on, for example, different patches worn by a given user, relative proximity/distance among the users wearing the respective patches, some hierarchy of the users and/or patches, or some combination thereof. In some embodiments, the communication links between the patches can be configured as a mesh network, or be based on such a network.

In some embodiments, a system of patches as described herein (e.g., in reference to FIGS. 19-23) can provide a system level information that may not be available from an individual patch.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional subcomponents to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Some aspects of the systems and methods described herein can advantageously be implemented using, for example, computer software, hardware, firmware, or any combination of computer software, hardware, and firmware. Computer software can comprise computer executable code stored in a computer readable medium (e.g., non-transitory computer readable medium) that, when executed, performs the functions described herein. In some embodiments, computer-executable code is executed by one or more general purpose computer processors. A skilled artisan will appreciate, in light of this disclosure, that any feature or function that can be implemented using software to be executed on a general purpose computer can also be implemented using a different combination of hardware, software, or firmware. For example, such a module can be implemented completely in hardware using a combination of integrated circuits. Alternatively or additionally, such a feature or function can be implemented completely or partially using specialized computers designed to perform the particular functions described herein rather than by general purpose computers.

Multiple distributed computing devices can be substituted for any one computing device described herein. In such distributed embodiments, the functions of the one computing device are distributed (e.g., over a network) such that some functions are performed on each of the distributed computing devices.

Some embodiments may be described with reference to equations, algorithms, and/or flowchart illustrations. These methods may be implemented using computer program instructions executable on one or more computers. These methods may also be implemented as computer program products either separately, or as a component of an apparatus or system. In this regard, each equation, algorithm, block, or step of a flowchart, and combinations thereof, may be implemented by hardware, firmware, and/or software including one or more computer program instructions embodied in computer-readable program code logic. As will be appreciated, any such computer program instructions may be loaded onto one or more computers, including without limitation a general purpose computer or special purpose computer, or other programmable processing apparatus to produce a machine, such that the computer program instructions which execute on the computer(s) or other programmable processing device(s) implement the functions specified in the equations, algorithms, and/or flowcharts. It will also be understood that each equation, algorithm, and/or block in flowchart illustrations, and combinations thereof, may be implemented by special purpose hardware-based computer systems which perform the specified functions or steps, or combinations of special purpose hardware and computer-readable program code logic means.

Furthermore, computer program instructions, such as embodied in computer-readable program code logic, may also be stored in a computer readable memory (e.g., a non-transitory computer readable medium) that can direct one or more computers or other programmable processing devices to function in a particular manner, such that the instructions stored in the computer-readable memory implement the function(s) specified in the block(s) of the flowchart(s). The computer program instructions may also be loaded onto one or more computers or other programmable computing devices to cause a series of operational steps to be performed on the one or more computers or other programmable computing devices to produce a computer-implemented process such that the instructions which execute on the computer or other programmable processing apparatus provide steps for implementing the functions specified in the equation(s), algorithm(s), and/or block(s) of the flowchart(s).

Some or all of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list. The word "exemplary" is used exclusively herein to mean "serving as an example, instance, or illustration." Any implementation described herein as "exemplary" is not necessarily to be construed as preferred or advantageous over other implementations.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A wearable patch comprising:
    a patch substrate configured to support a plurality of components, and to allow the patch to be attached to a skin of a user;
    an alert component implemented relative to the patch substrate and configured to generate and provide an alert output to the skin of the user based on an alarm control signal; and
    a receiver circuit in communication with the alert component and configured to receive the alarm control signal and induce the generation of the alert output by the alert component.

2. The wearable patch of claim 1 wherein the alert component includes a micro-transducer having a driver circuit and an alert element, the driver circuit configured to receive the alarm control signal and generate a drive signal for the alert element for the generation of the alert output.

3. The wearable patch of claim 2 wherein the driver circuit and the alert element are configured such that the alert output includes a sound output.

4. The wearable patch of claim 3 wherein the driver circuit and the alert element are configured such that the sound output has an intensity selected to awake the user from a sleeping state, but sufficiently low so that another sleeping person near the user is not awakened by the sound output.

5. The wearable patch of claim 2 wherein the driver circuit and the alert element are configured such that the alert output includes a vibration output.

6. The wearable patch of claim 2 wherein the driver circuit and the alert element are configured such that the alert output includes an electrical output.

7. The wearable patch of claim 2 wherein the driver circuit and the alert element are configured such that the alert output includes an output having a uniform intensity.

8. The wearable patch of claim 2 wherein the driver circuit and the alert element are configured such that the alert output includes an output having a continuously varying intensity.

9. The wearable patch of claim 2 wherein the driver circuit and the alert element are configured such that the alert output includes an output having a pattern of intensity pulses.

10. The wearable patch of claim 9 wherein the pattern of intensity pulses includes a plurality of periodic pulses having an approximately same intensity value.

11. The wearable patch of claim 9 wherein the pattern of intensity pulses includes a repeating sets of pulses, each set including a plurality of different intensity pulses.

12. The wearable patch of claim 9 wherein the pattern of intensity pulses includes a plurality of pulses having random or pseudo-random intensity values.

13. The wearable patch of claim 1 wherein the patch substrate includes an adhesive layer configured to allow the wearable patch to stick to the skin of the user.

14. The wearable patch of claim 13 wherein the patch substrate is dimensioned to be worn on an arm of the user.

15. The wearable patch of claim 13 wherein the patch substrate is dimensioned to be worn on an earlobe of the user.

16. The wearable patch of claim 1 wherein at least the receiver circuit is implemented as an RFID (radio-frequency identification) circuitry.

17. A method for alerting a person, the method comprising:
    receiving, with a receiver of a wearable patch attached to a skin of the person, an alarm control signal;
    generating, with a driver circuit, a drive signal in response to the control signal; and
    generating, with an alert element, an alert output based on the drive signal, such that the alert output is provided to the skin of the person to thereby alert the person.

18. A system for alerting a person, the system comprising:
    a wearable patch configured to be attached to a skin of the person and alert the person with an alert output provided to the skin of the person based on an alarm control signal; and
    a control unit configured to generate and transmit the alarm control signal to the wearable patch.

19. The system of claim 18 wherein the wearable patch includes an RFID (radio-frequency identification) circuitry configured to receive the alarm control signal from the control unit.

20. The system of claim 19 wherein the wearable patch further includes a micro-transducer configured to generate the output based on the alarm control signal.

* * * * *